(12) United States Patent
Stubbs

(10) Patent No.: US 8,828,008 B2
(45) Date of Patent: Sep. 9, 2014

(54) APPARATUS FOR ARTHROSCOPIC ASSISTED ARTHROPLASTY OF THE HIP JOINT

(76) Inventor: Allston J. Stubbs, Winston-Salem, NC (US)

(*) Notice: Subject to any disclaimer, the term of this patent is extended or adjusted under 35 U.S.C. 154(b) by 1154 days.

(21) Appl. No.: 12/398,960

(22) Filed: Mar. 5, 2009

(65) Prior Publication Data

US 2009/0281545 A1    Nov. 12, 2009

Related U.S. Application Data

(60) Provisional application No. 61/034,066, filed on Mar. 5, 2008.

(51) Int. Cl.
| | | |
|---|---|---|
| *A61B 17/58* | (2006.01) | |
| *A61B 17/17* | (2006.01) | |
| *A61F 2/34* | (2006.01) | |
| *A61F 2/46* | (2006.01) | |
| *A61B 17/16* | (2006.01) | |
| *A61F 2/30* | (2006.01) | |

(52) U.S. Cl.
CPC ..... *A61B 17/1703* (2013.01); *A61F 2002/4631* (2013.01); *A61F 2002/4635* (2013.01); *A61B 17/1666* (2013.01); *A61F 2002/30299* (2013.01); *A61F 2002/30579* (2013.01); *A61F 2/34* (2013.01); *A61B 17/1746* (2013.01); *A61B 17/1721* (2013.01); *A61F 2230/0093* (2013.01); *A61F 2/4609* (2013.01)
USPC .................... 606/87; 606/89; 606/91; 606/81

(58) Field of Classification Search
USPC ................ 606/87–91, 81, 84, 85; 623/22.12, 623/22.15
See application file for complete search history.

(56) References Cited

U.S. PATENT DOCUMENTS

| | | | | |
|---|---|---|---|---|
| 2,537,070 | A * | 1/1951 | Longfellow | 606/67 |
| 5,429,641 | A * | 7/1995 | Gotfried | 606/67 |
| 5,514,143 | A * | 5/1996 | Bonutti et al. | 606/86 R |
| 5,527,338 | A * | 6/1996 | Purdy | 606/200 |
| 5,725,593 | A * | 3/1998 | Caracciolo | 623/22.23 |
| 5,944,738 | A * | 8/1999 | Amplatz et al. | 606/213 |
| 6,080,155 | A * | 6/2000 | Michelson | 606/86 A |
| 6,482,237 | B2 * | 11/2002 | Mosseri | 623/22.12 |
| 6,989,019 | B2 * | 1/2006 | Mazzocchi et al. | 606/200 |
| 2003/0004513 | A1 * | 1/2003 | Guzman et al. | 606/62 |
| 2003/0105467 | A1 * | 6/2003 | Ralph et al. | 606/90 |
| 2004/0225294 | A1 * | 11/2004 | Frederick et al. | 606/81 |
| 2005/0143745 | A1 * | 6/2005 | Hodorek et al. | 606/87 |
| 2005/0149050 | A1 * | 7/2005 | Stifter et al. | 606/102 |

OTHER PUBLICATIONS

Kelly et al., "Hip Arthroscopy: Current Indications, Treatment Options, and Management Issues", *Am. J. Sports Med.*, 2003, pp. 1020-1037, vol. 31, No. 6, (Nov. 2003).

* cited by examiner

*Primary Examiner* — Paul Prebilic
(74) *Attorney, Agent, or Firm* — Womble Carlyle Sandridge & Rice, LLP

(57) ABSTRACT

Devices, systems and methods for performing arthroscopic evaluations and procedures in and near the hip joint are provided. An arthroscopic assisted arthroplasty system is useful in the treatment of arthritic hip conditions, conserving healthy tissue, and limiting iatrogenic injury associated with traditional surgical exposures. A guide wire system employing retrograde and antegrade reamers along the femoral neck is useful in anatomic placement of instrumentation without formal hip dislocation. Fluoroscopy and computer assisted navigation enhance the system, methods, and apparatus. Acetabular and femoral collapsible prosthetic forms are useful in arthroscopic assisted placement. The devices, systems, and methods are effective to assist an operating surgeon in the addressing mild to moderate arthritic conditions of the femoral head and acetabulum where tissue conservation and surgical exposure morbidities should be limited.

26 Claims, 11 Drawing Sheets

APPARATUS FOR ARTHROSCOPIC ASSISTED ARTHROPLASTY OF THE HIP JOINT

CROSS-REFERENCE TO RELATED APPLICATIONS

This application claims the benefit of U.S. Provisional Patent Application Ser. No. 61/034,066 filed Mar. 5, 2008, the contents of which are incorporated herein by reference.

BACKGROUND OF THE INVENTION

1. Field of the Invention

This invention relates to devices, systems and methods for arthroscopic examination and treatment and surgical examination and treatment, particularly in and near the hip joint. In particular, the invention relates to arthroscopic devices, systems and methods for performing arthroplasty of the hip joint and the region near to the hip joint, including computer and robotic assisted surgical navigation, and for resurfacing and other partial arthroplasty treatments in and near the hip joint.

2. Description of Related Art

The hip is vital to human locomotion, and hip injuries and diseases can significantly impact the ability of a patient to carry out day-to-day tasks as well as impair the performance of athletes and active amateur sports enthusiasts. Hip conditions impairing movement or causing pain with normal activity may result from trauma, age, or disease conditions.

Hip surgery is indicated where there is injury or change in the hip joint requiring removal or reshaping of bone or cartilage or of material present in the joint. Arthroscopic surgery causes the least amount of ancillary trauma and allows for more rapid recovery than do other forms of hip surgery. Arthroscopic treatment of the hip is discussed, for example, in Kelly et al., "Hip Arthroscopy: Current Indications, Treatment Options, and Management Issues," American Journal of Sports Medicine 31(6):1020-1037 (2003). Hip joint replacement or hip joint arthroplasty is the partial or full substitution of the joint components with synthetic/man-made/biocompatible materials. Hip joint arthroplasty is generally performed when the function of the native joint is compromised by significant pain, loss of congruency, cartilage/bone loss, and lack of motion.

Osteoarthritis (OA) and its precursor chondromalacia are common diseases of the hip joint. Both conditions typically are a function of age, genetics, prior injury, and underlying joint pathomechanics. Treatment of significant chondromalacia and osteoarthritis is typically performed via an arthroplasty procedure where the diseased joint surface and surrounding bone is replaced with durable biocompatible materials, most commonly, metal alloys, plastic polymers, and ceramics, and, less frequently, organic and inorganic tissue replacements or scaffolds.

Arthroplasty procedures are performed throughout the world and are most commonly done on the hip joint. Arthroplasty techniques are varied, but share the same goal of removing the dysfunctional arthritic joint areas and replacing them with materials that preserve joint function. Specifically, hip arthroplasty procedures are intended to give the patient recipient a pain-free weight bearing joint whose motion replicates the native hip joint.

Arthroplasty procedures of the hip joint specifically target disease of the femoral head (ball portion) and acetabulum (socket portion). Traditional total hip replacement surgery amputates the femoral head and a portion of the femoral neck as well as the acetabulum. Resurfacing-type procedures amputate a portion of the femoral head as well as the acetabulum. Partial resurfacing procedures typically result in a portion of the femoral head being resected. Substituted in their place are materials that possess durability and function.

Surgical techniques to accomplish arthroplasty goals require an open rather than an arthroscopic approach. These open approaches may involve traditional full incision exposures such as the Smith-Peterson, Hardinge, or Watson Jones, or newer more limited incision exposures based on the traditional approaches such as the two-incision, mini-incision, and muscle splitting/sparing options. Regardless of the approach selected, open surgery is performed, resulting in greater iatrogenic soft tissue trauma.

The most common arthroscopic approach to the hip is from the anterior aspect of the thigh. The two arthroscopic portals from this approach are the anterior/mid anterior and anterior-lateral. Occasionally, other portals are utilized including the accessory lateral portal and posterior-lateral portal. Typically, a hip arthroscopy involves procedures within two compartments, the central and the peripheral. From the central compartment, the surgeon can address pathology of the labral and articular cartilages, the synovium point lining), and acetabular rim. From the peripheral compartment, the surgeon can address pathology of the femoral head and femoral neck junction. In addition to the central and peripheral compartments, extra-articular compartments exists about the region of the lesser and greater trochanters.

Although arthroscopic examination, evaluation, and treatment of the hip and hip region are common procedures, there is not a method or system for arthroscopic assisted hip joint arthroplasty. There is, therefore, a specific need for improved devices and methods and for improved arthroplasty treatments which lower the risk of iatrogenic injury, postoperative complications, and provide improved means for performing arthroscopic hip treatments and procedures.

BRIEF SUMMARY OF THE INVENTION

This invention relates to devices, systems and methods for arthroscopic examination and treatment, particularly for medical procedures in and near a hip joint of a patient. The devices may be disposable, single use arthroscopic or reusable, multi use devices. The devices, systems and methods disclosed herein are useful for the partial or complete arthroplasty of the hip joint via arthroscopic and computer navigated applications. Embodiments of the devices, systems and methods are effective to assist an operating surgeon in the assessment of hip cartilage injury and treatment of recognized injury via substitution of biocompatible materials.

In an embodiment, the present invention provides an arthroscopic method and instrumentation for a hip procedure involving replacement of diseased joints having a system of distraction, visualization, computer assisted/guided navigation of instruments and implants, reaming/osteotomy, fixation, and placement of arthroplasty components which serve to facilitate accurate removal of diseased tissue and ensure precise placement of arthroplasty materials.

The distraction system comprises a three or four pin external fixation apparatus that expands and modifies the operative space between the anatomic femoral head and acetabulum. Typically, two pins are placed along the proximal femur and one or two pins are placed along the acetabulum. Traction placed along the operative hip via a traction table or manually is secured using the external fixation system. The external fixation system may exist as a uniplanar or multiplanar system with angular rotational capability to facilitate instrumentation placement, surgical effects, or implant placement. The external fixation system has the capability of supporting extra-corporal or intra-corporal navigation aides such as radio frequency identification (RFID) and reflector/reflecting markers.

The visualization system comprises a high flow, pressure regulated fluid pump which maintains transparent visualization for the hip arthroscope via arthroscopic cannulae placed about the hip joint and along the retrograde femoral neck access. The direct arthroscopic visualization may be enhanced by the use of computer navigated software and hardware that guides instrument placement, surgical effects, or implant placement.

The reaming system comprises a device for performing a retrograde technique facilitated by a guide pin/wire. The guide pin/wire is placed under the assistance of fluoroscopy, direct arthroscopic visualization, and/or computer assisted navigation. The series of retrocentripetal reamers is cannulated to accommodate the guide pin/wire. The cephalad aspect of the reamers deploys in a centripetal manner allowing distinctive contact of the reamer with the bone of both the femoral head and acetabulum. Each reamer possess a distinctive deployment angle which directs the angle of the cutting surface along the bone surface. The reaming apparatus may be used with or without the guide wire (i.e., free-handed). The reaming apparatus may be guided via computer assisted navigation. The femoral head is contoured via a series of successive osteotomies approximating 0 degrees, 80 degrees, and 45 degrees from the relative horizontal. The acetabular reaming system will be antecentripetal and will radially osteotomize the acetabular space proper and the acetabular rim.

The fixation system comprises techniques of press (wedge) fit, polymethylmethacrylate (PMMA), screw fixation, and tension banding. Both the femoral and acetabular components accept press fit techniques or cementing. The cement system will provide for injection or vacuum placement of PMMA along the bone-implant interface. The retrograde nature of the femoral access allows unique combinations of screw fixation and tension banding about the peritrochanteric space.

The components of both the femoral head and acetabulum are highly polished geodesic aperture umbrella prosthetics. Being like an umbrella, the prosthetic can be transferred along the retrograde femoral neck access into the joint space. The aperture property ensures proper radial deployment. The geodesic construct ensures high rigidity and durability. Once placed, components can be polished/melded in vivo.

BRIEF DESCRIPTION OF THE SEVERAL
VIEWS OF THE DRAWING(S)

Figures 3A, 3B:
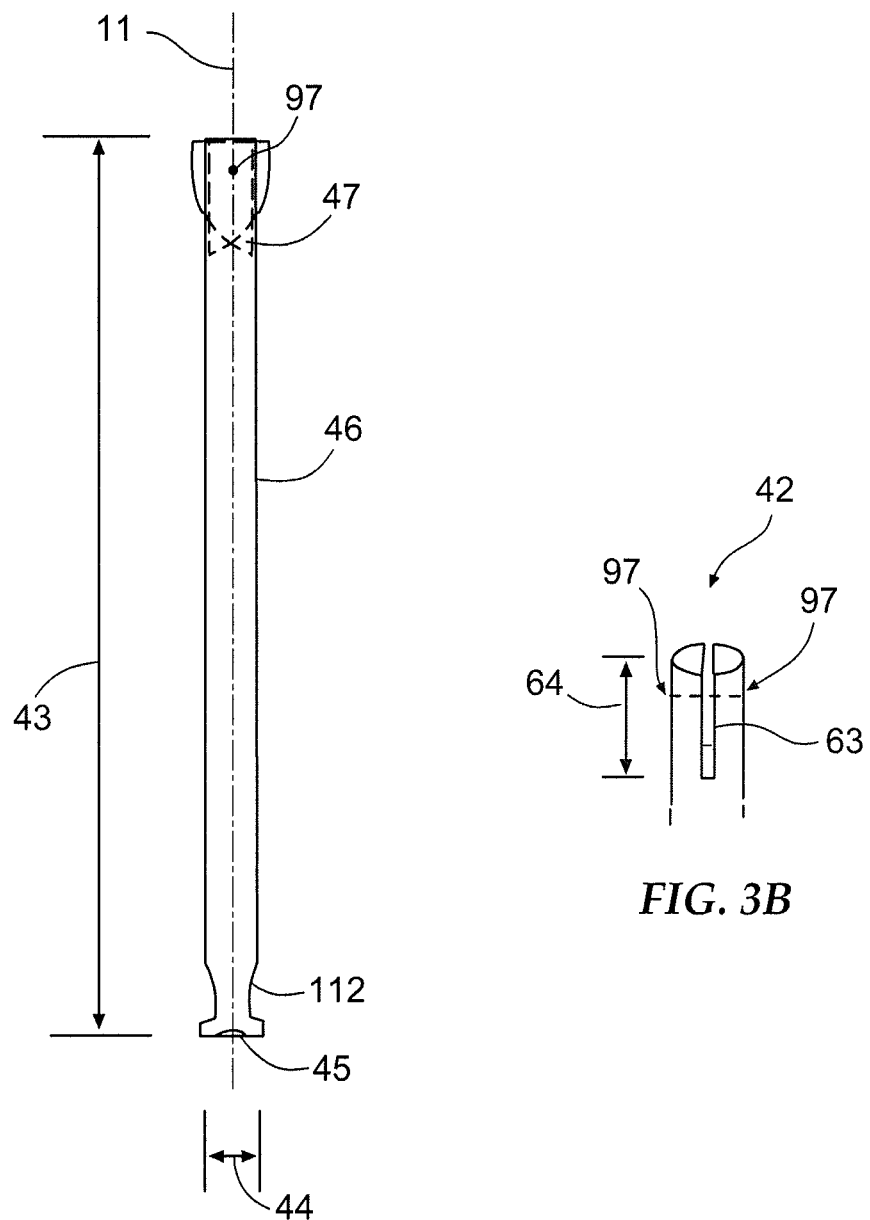

FIG. 3A shows a schematic view of an arthroscopic transfemoral retrocentripetal and antecentripetal radial reamer having features of the invention including cannulated guide tube containing reamer blades stored in a retracted or enclosed format and deployable via centripetal force or central deployment rod or wire. The cutting surface of the reamer blades act in a retrograde or antegrade manner and assume variable angles and shapes.

FIG. 3B is a schematic illustration of a tip portion of an antegrade and retrograde reamer of FIG. 3A in which there is a supporting slot and axis for the cutting blades.

FIG. 3C shows a schematic view of an arthroscopic transfemoral retrocentripetal and antecentripetal radial reamer having features of the invention including cannulated guide tube containing reamer blades in a deployed position and deployable via centripetal force or central deployment rod or wire. The cutting surface of the reamer blades act in a retrograde or antegrade manner and assume variable angles and shapes.

FIG. 3D shows a schematic view of an arthroscopic transfemoral retrocentripetal and antecentripetal radial reamer having features of the invention including cannulated guide tube containing a reamer blade stored in a retracted or enclosed format and deployable via centripetal force or central deployment rod or wire coupled to the blade. The cutting surface of the reamer blades act in a retrograde or antegrade manner and assume variable angles and shapes.

FIG. 3E is a schematic illustration of a tip portion of an antegrade and retrograde reamer of FIG. 3D in which there is a supporting slot for the cutting blade.

Figure 3F:
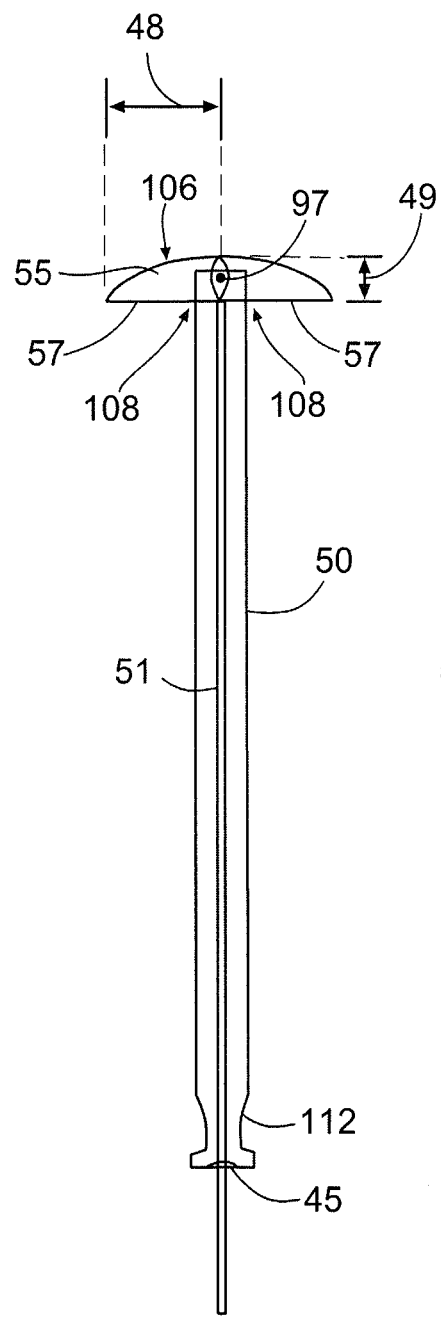
Figure 3F:
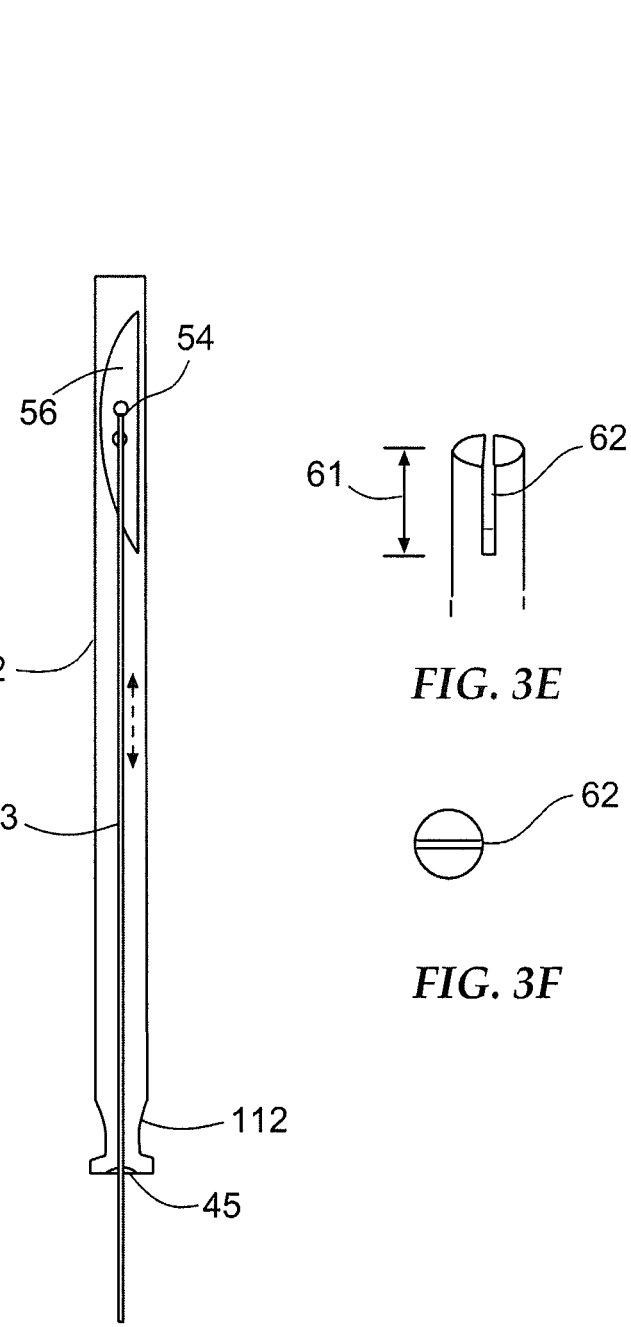

FIG. 3F is a schematic illustration of a tip portion of an antegrade and retrograde reamer of FIG. 3D in which there is a supporting slot for the cutting blade.

Figures 3G, 3H:
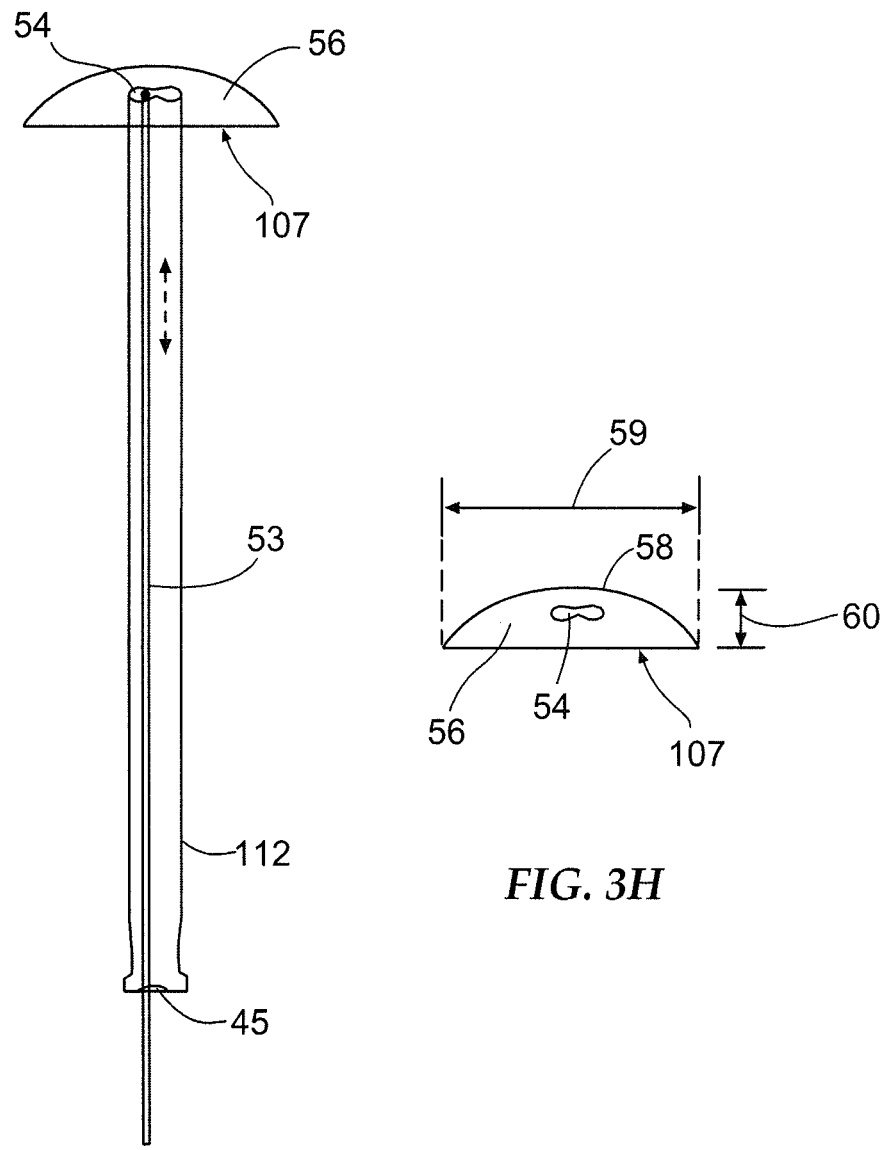

FIG. 3G shows a schematic view of an arthroscopic transfemoral retrocentripetal and antecentripetal radial reamer having features of the invention including cannulated guide tube containing a reamer blade deployed via centripetal force or central deployment rod or wire coupled to the blade. The cutting surface of the reamer blade acts in a retrograde or antegrade manner and assumes variable angles and shapes.

FIG. 3H is a schematic illustration of a reamer blade portion of an antegrade and retrograde reamer of FIG. 3G having features of the invention including a coupling slot, a variable antegrade cutting surface, and a variable retrograde cutting surface.

Figure 4A:
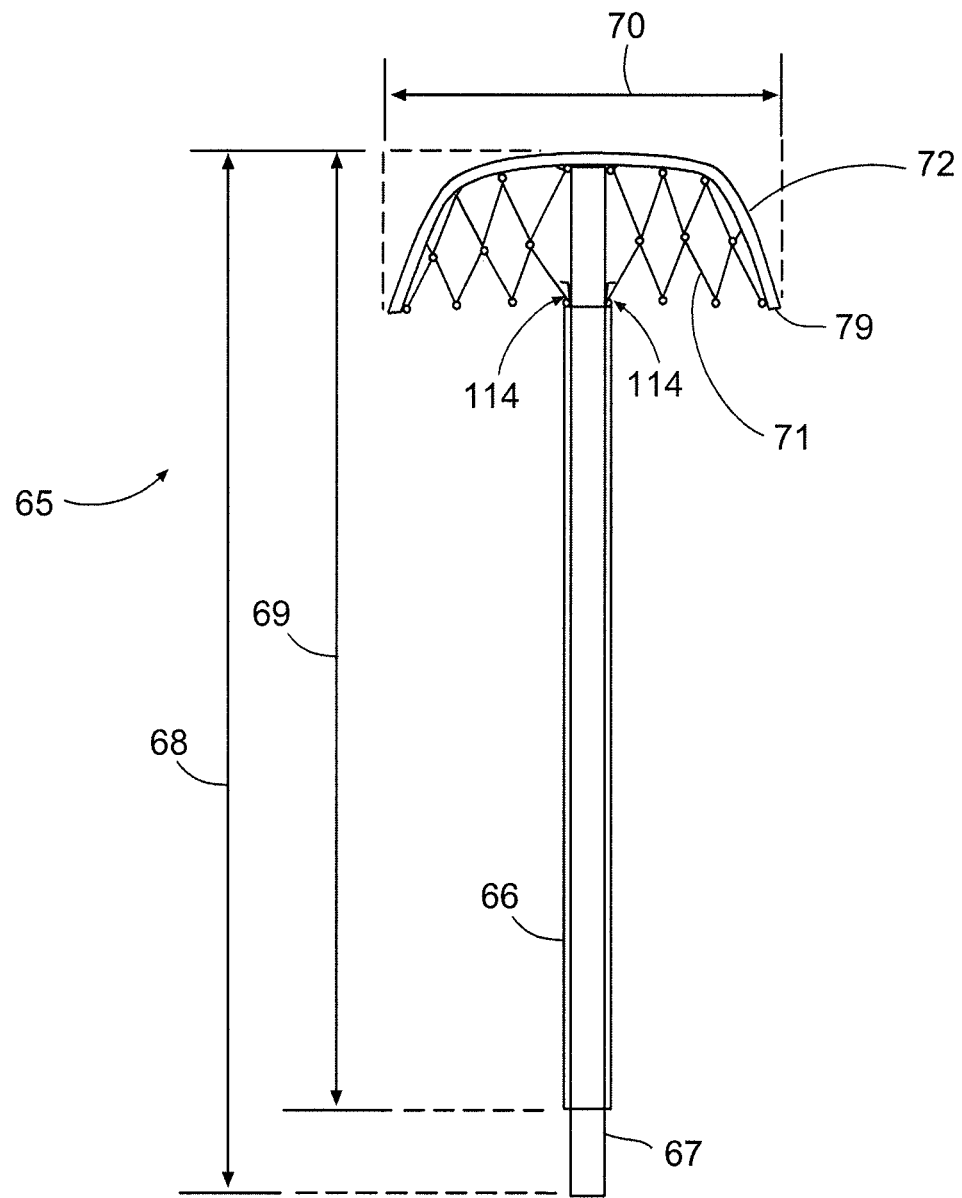

FIG. 4A shows a schematic view of an arthroscopic transfemoral acetabular prosthesis and deployment rod and sleeve having features of the invention including collapsible and expandable forms to allow passage along the femoral neck access.

Figure 4B:
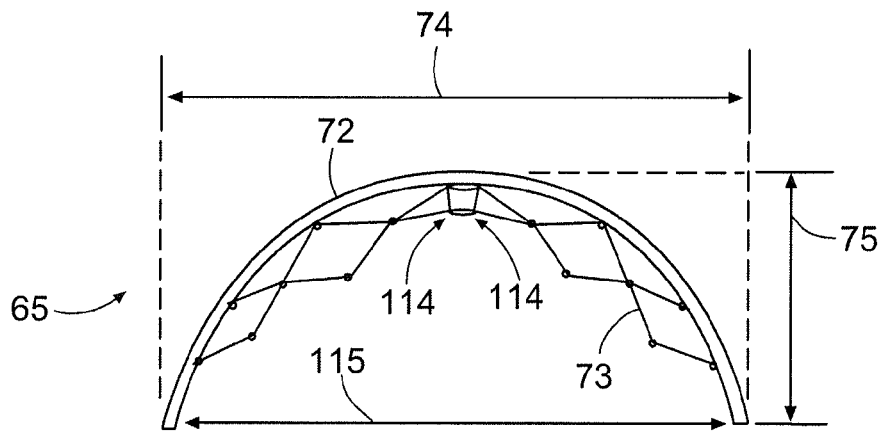

FIG. 4B shows a schematic illustration of an arthroscopic transfemoral acetabular prosthesis having features of the invention including a clad design configured with outer and inner shells utilizing a "Hoberman umbrella" type truss system to develop a hemispheric like form. This prosthetic hemisphere form can be tensioned, locked, and secured to the acetabulum. The acetabular prosthetic hemisphere form is congruent with the femoral prosthetic form. The space between the prosthetic shells will permit delivery of PMMA cement to prosthetic-bone interface or other biocompatible/osteoinductive structural matrix/filler.

Figure 4C:
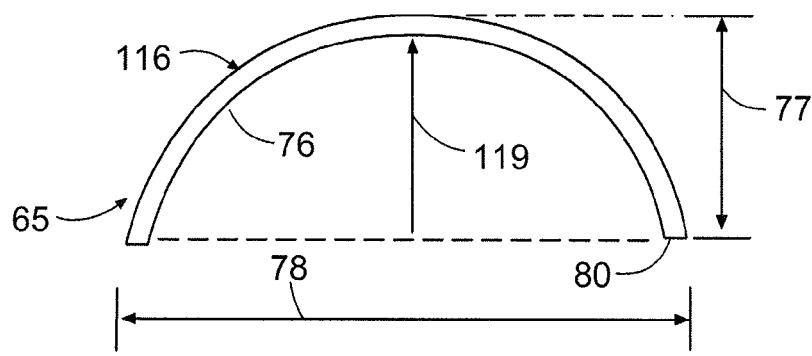

FIG. 4C is a schematic illustration of the acetabular liner portion of an arthroscopic transfemoral acetabular prosthesis having features of the invention including a collapsible shape which is congruent with the femoral prosthetic form.

Figure 4D:
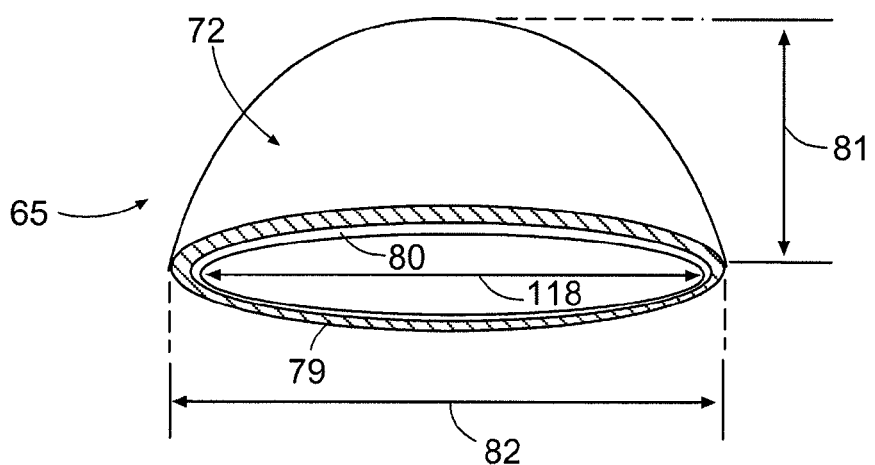

FIG. 4D shows a schematic illustration of an arthroscopic transfemoral acetabular prosthesis having features of the invention including a clad design configured with outer and inner shells utilizing a Hoberman umbrella type truss system to develop a hemispheric like form. This prosthetic hemisphere form can be tensioned, locked, and secured to the acetabulum. The acetabular prosthetic hemisphere form is congruent with the femoral prosthetic form. The space between the prosthetic shells will permit delivery of PMMA cement to prosthetic-bone interface or other biocompatible/osteoinductive structural matrix/filler.

Figure 5A:
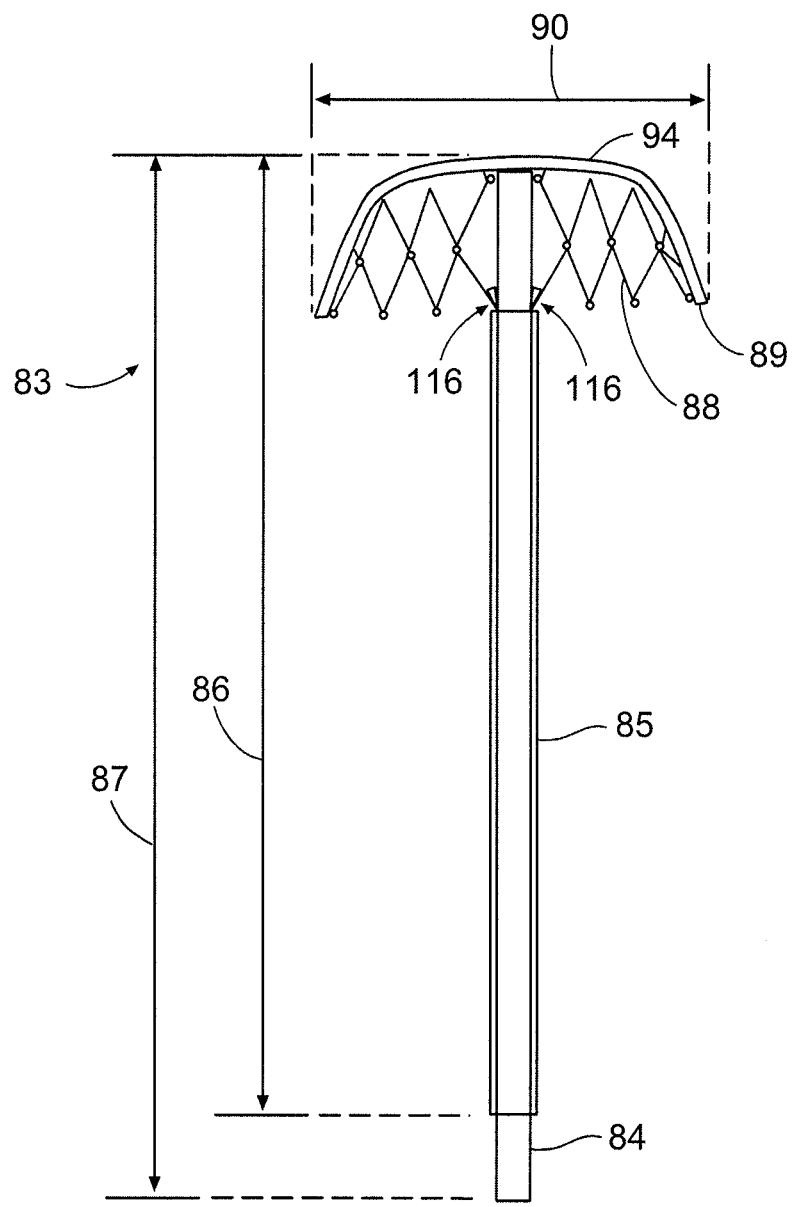

FIG. 5A is a schematic illustration of a femoral head prosthesis and deployment rod and sleeve having features of the invention including collapsible and expandable forms to allow passage along the femoral neck access.

Figure 5B:
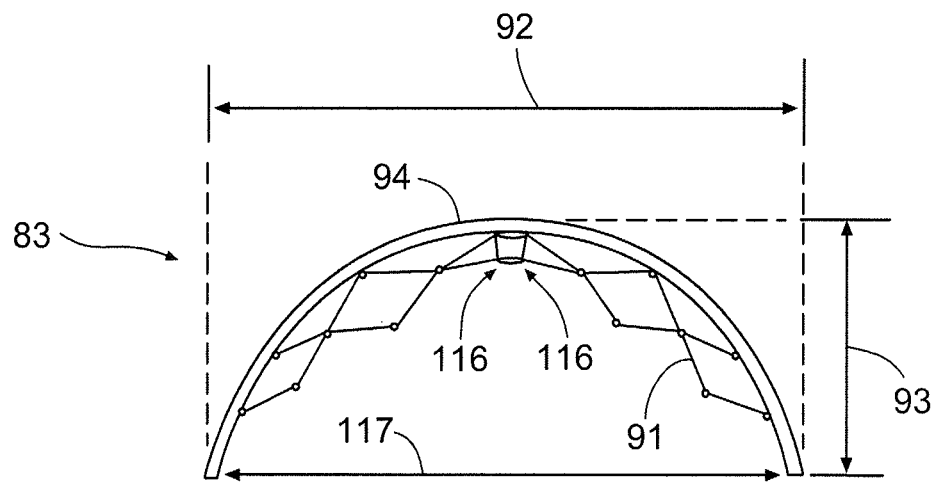

FIG. 5B is a schematic illustration of an arthroscopic transfemoral femoral prosthesis having features of the invention including a clad design configured with outer and inner shells utilizing a "Hoberman umbrella" type truss system to develop a hemispheric like form. This prosthetic hemisphere form can be tensioned, locked, and secured to the femoral neck. The femoral prosthetic hemisphere form is congruent with the acetabular prosthetic form. The space between the truss system and the bone will permit delivery of PMMA cement to prosthetic-bone interface or other biocompatible/osteoinductive structural matrix/filler.

Figure 5C:
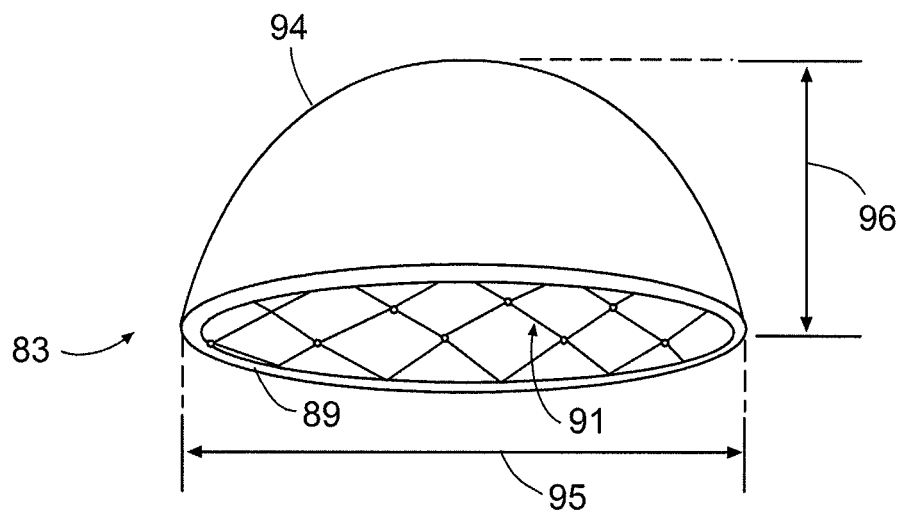

FIG. 5C is a schematic illustration of an arthroscopic transfemoral femoral prosthesis having features of the invention including a clad design configured with outer and inner shells utilizing a "Hoberman umbrella" type truss system to develop a hemispheric like form. This prosthetic hemisphere form can be tensioned, locked, and secured to the femoral neck. The femoral prosthetic hemisphere form is congruent with the acetabular prosthetic form. The space between the truss system and the bone will permit delivery of PMMA cement to prosthetic-bone interface or other biocompatible/osteoinductive structural matrix/filler.

DETAILED DESCRIPTION OF VARIOUS EMBODIMENTS OF THE INVENTION

The field of hip arthroscopy is increasing to include procedures which modify both the bone and soft tissue structures of the hip. Traditional arthroplasty of the hip joint is a common procedure. Currently, there is no practical method or device to perform arthroplasty of the hip joint without an open surgical procedure. To the orthopaedic surgeon treating diseased hip joints, a reliable arthroscopic method to resect diseased joint surfaces and substitute biocompatible materials in a tissue conserving way would be important in patients where the limitations of a traditional open joint replacement namely exposure and bone loss would favor a tissue sparing approach.

Apparatus

The system includes instruments and tools capable of accessing and modifying the intra-articular space of the hip via a passage along the femoral neck. Additional access to the hip joint can be maintained through other arthroscopic joint portals. Arthroscopic visualization of the diseased joint space can be carried out using a fracture table or external fixator distraction. The system is guide wire localized and executed via cannulated instruments under fluoroscopy, and, if indicated, via computer surgical navigation. Intra-articular shaping of the bone is performed with centripetal reamers which act retrograde on the femur and antegrade on the acetabulum. Arthroplasty components are introduced through the femoral neck access and deployed in the pre-reamed spaces. Preferably, the system employs disposable, single use modular components. Computer assisted surgical navigation is compatible and complementary with the methods and apparatus of this invention and may be used to facilitate hip joint surgical access, instrument placement, bone and soft tissue resection, and implant placement.

Method

The hip joint is a major weight bearing joint of the mammalian body. Hip joint degenerative disease such as osteoarthritis may be an end stage process necessitating removal of diseased bone and soft tissue and replacement of removed tissue with biocompatible materials. Traditional methods of hip joint osteoarthritis treatment via arthroplasty involve open surgical access to the hip joint via traditional and limited surgical incisions. Direct visualization through these incisions facilitates surgical decision making, removal of diseased tissue, and implantation of biocompatible replacement materials. The present invention utilizes indirect visualization of the surgical field via hip arthroscopy to facilitate surgical decision making, removal of diseased tissue, and implantation of biocompatible replacement materials. The utilization of hip arthroscopy rather than open surgical approaches for hip arthroplasty may result in less surgical morbidity to the patient secondary to less iatrogenic trauma, shorter hospitalization, and faster rehabilitation and recovery.

In use, the hip arthroscopy assisted arthroplasty system can be used on any patient with hip disease necessitating tissue removal and subsequent arthroplasty replacement. Access with the system is ensured via a hip distraction system of either a traction table or external skeletal fixation. Hip arthroscopy access is performed via traditional or modified surgical portal sites. The access system relies on retrograde guide wire/pin placement along the femoral neck. When needed, fluoroscopic imaging or computer assisted surgical navigation may be used to place the guide wire/pin. Bone and soft tissue resection by anatomically specific reamers for the femoral head and acetabulum is performed along the guide wire tract/canal. Biocompatible implant sizing and placement is done via placement along the guide wire tract/canal. The end product of the system is a stable hip joint arthroplasty which provides pain relief and hip joint function.

Application

The systems, apparatus and methods of the present invention are particularly useful for hip pathologies in which the operating surgeon considers the hip joint condition necessitating arthroplasty treatment. Such hip pathologies include but are not limited to osteochondral defects/lesions, avascular necrosis, slipped capital femoral epiphysis, fracture-dislocation, end stage inflammatory arthritis, and osteoarthritis. While patient age is not a defining aspect of the application of this invention, younger patients may find the arthroscopic methods and approach more appealing over traditional arthroplasty alternatives. It will be understood that the systems, apparatus and methods disclosed herein may also find use in other medical procedures and therapeutic applications as well.

Definitions

Where the singular is used, it is to be understood that plural is also included, so that, for example, the terms "a guide" and "a reamer" include and refer equally to multiple guides and reamers as well as to a singular guide and a singular reamer.

As used herein, the terms "movable" and "flexible" refer to the ability of the object modified by such terms to alter or have altered, its position, such as its relative position with respect to another object, or to alter, or have altered, its shape.

As used herein, the term "connective tissue" refers to ligaments (which connect bone to bone) and tendons (which connect muscle to bone). Cartilage and cartilaginous structures, such as cartilage covering femur and pelvic bone in the hip joint, are included in the term "connective tissue."

As used herein, the terms "bone" and "bone tissue" refer to the bones of a mammalian patient.

As used herein, the terms "muscle" and "muscle tissue" refer to skeletal and smooth muscle of a mammalian patient.

As used herein, the term "vascular tissue" refers to blood vessels and includes arterial and venous tissues and capillaries. Arterial vessels carry oxygenated blood from the heart and lungs to tissues, while venous vessels carry oxygen-depleted blood from the tissues to the heart and lungs. Capillaries are small vessels connecting the arterial with the venous system, and are the locus where oxygen transfer from blood to tissue typically occurs.

As used herein, the term "hip arthroscopy or hip arthroscope" refers to a surgical visualization system of the hip joint comprising a light source and a camera which can project, capture, and transmit surgical field images.

As used herein, the term "hip arthroplasty" refers to the surgical resection and replacement of hip joint tissue with synthetic, biologic (autograft or allograft), or biocompatible materials such as metal, plastic, ceramic, or engineered tissue.

As used herein, the term "hip joint" refers to the anatomic hip joint (femoral head and acetabulum) and surrounding muscle, neural, and vascular structures.

As used herein, the term "cannulated" refers to the properties of a tool or device containing a single central lumen/tract or multiple lumens/tracts to facilitate placement over a guide wire or placement of an assisting instrument.

As used herein, the term "fluoroscopy" refers to the use of X-ray radiation to project images of whole or partial body tissues, instruments, and implants not directly visible to the human eye or surgical device such as an arthroscope.

As used herein, the term "computer assisted surgery or computer navigated surgery" refers to the used of a computer system to directly or indirectly assist the placement and control of surgical instruments and tools for the purpose of tissue assessment, removal, and replacement. The system may rely on RFID or position markers which report patient, instrument, and implant locations to operating surgeon or external monitor.

As used herein, the term "radiofrequency identification or RFID" refers to a system of a specific location device which has been permanently or temporarily implanted to convey position information to a local or distant terminal for interpretation.

Devices, systems and methods disclosed herein provide improvements in tools and methods useful for arthroscopic examination and treatment, particularly in and near a hip joint. The devices are suitable for arthroscopic procedures, are, with the exception of arthroplasty implants, preferably disposable, and provide a unique combination of arthroscopic hip joint access, tissue removal/modification, and arthroplasty implants.

Figure 1A:
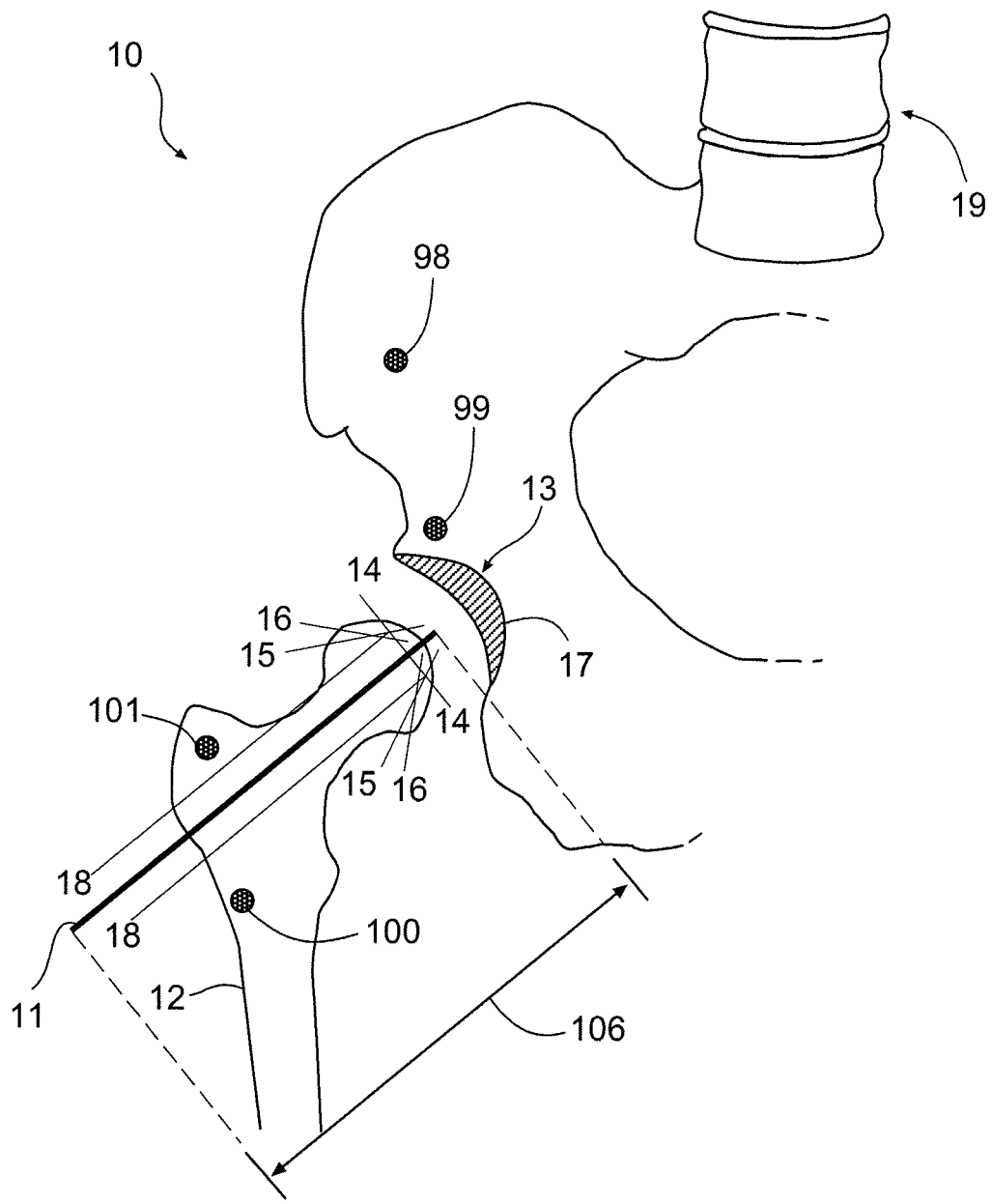
FIG. 1A shows a schematic view of a hemipelvis pre-implant cross-section having features of the invention including transfemoral guide pin, computer assisted navigation capability along external fixation distractor, transfemoral femoral preparation, and transfemoral acetabular preparation.

A hemipelvis pre-operative cross-sectional layout of the arthroscopically assisted arthroplasty system 10 is illustrated in FIG. 1A. Systems having features of the invention, such as a system 10 as illustrated in FIG. 1A, may include femur 12, acetabulum 13, lumbar spine 19, acetabular external fixation and navigation sites 98 & 99, femoral external fixation and navigation sites 100 & 101, femoral guide wire/pin 11, femoral neck 18, planned femoral osteotomy cut at 90 degrees to the pin 14, planned femoral osteotomy cut at 20 degrees to the pin 15, planned femoral osteotomy cut at 45 degrees to the pin 16, and planned acetabular reaming 17. The dimensions of the femoral pin 106 may be about 80 mm to about 300 mm in length and about 1 mm to about 5 mm in diameter.

Figure 1B:
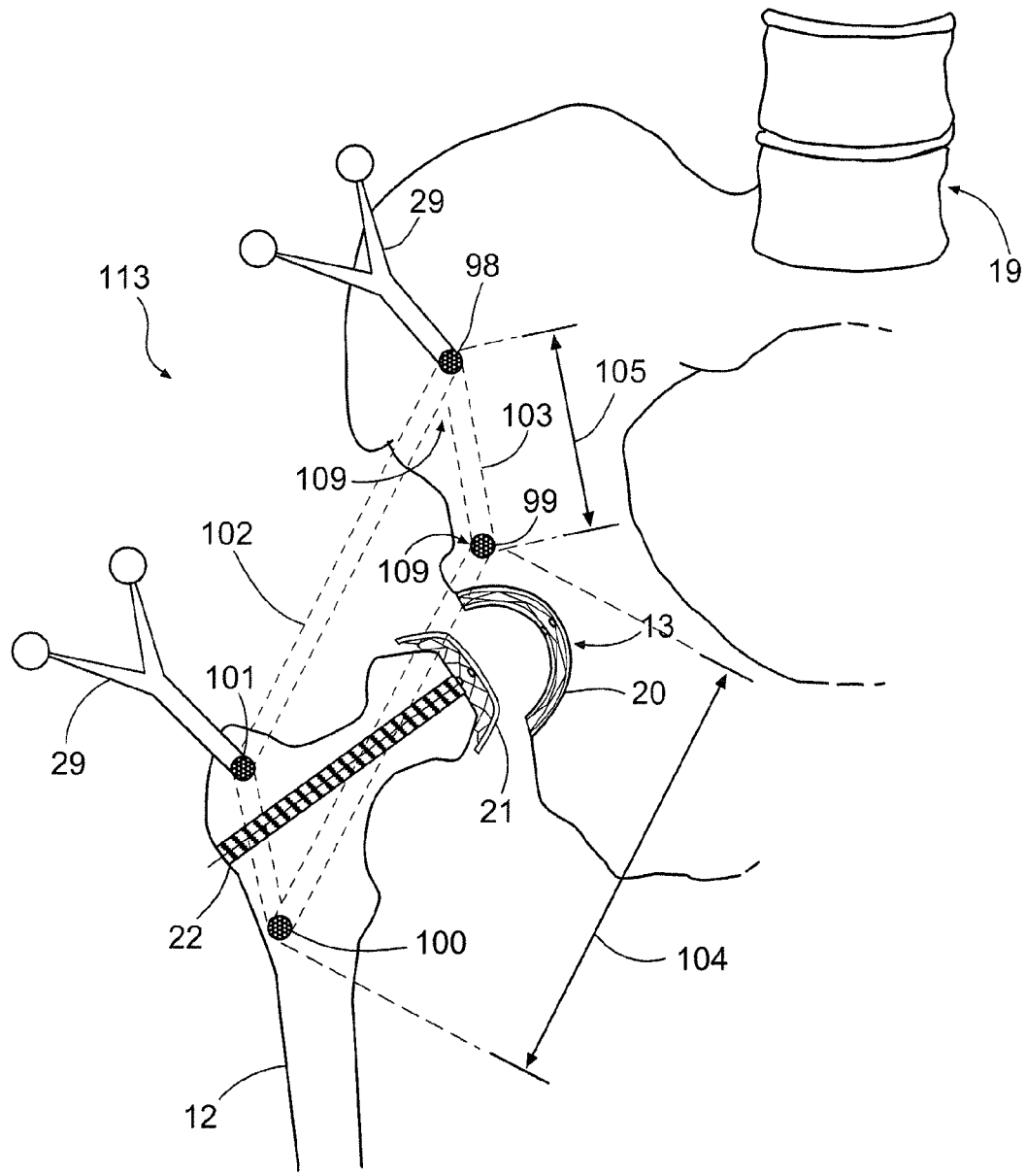
FIG. 1B shows a schematic view of a hemipelvis post-implant cross-section having features of the invention including transfemoral access tunnel, computer assisted navigation capability along external fixation distractor, transfemoral femoral component placement, and transfemoral acetabular component placement.

A hemipelvis post-operative cross-sectional layout of the arthroscopically assisted arthroplasty system 113 is illustrated in FIG. 1B. Systems having features of the invention, such as a system 113 as illustrated in FIG. 1B, may include femur 12, acetabulum 13, lumbar spine 19, acetabular external fixation and navigation sites 98 & 99, femoral external fixation and navigation sites 100 & 101, femoral neck access 22, arthroscopic transfemoral femoral prosthesis 21, arthroscopic transfemoral acetabular prosthesis 20, computer assisted navigation capability 29, external fixation system 102 & 103. The dimensions of the external fixation system medial to lateral bars 104 may be about 50 mm to about 250 mm in length and about 2 mm to about 10 mm in diameter. The dimensions of the external fixation system cranial to caudal bars 105 may be about 20 mm to about 200 mm in length and about 2 mm to about 10 mm in diameter. The shape of the external fixation system may approximate any geometrical configuration and angle 109 that allows hip joint distraction.

Figure 2A:
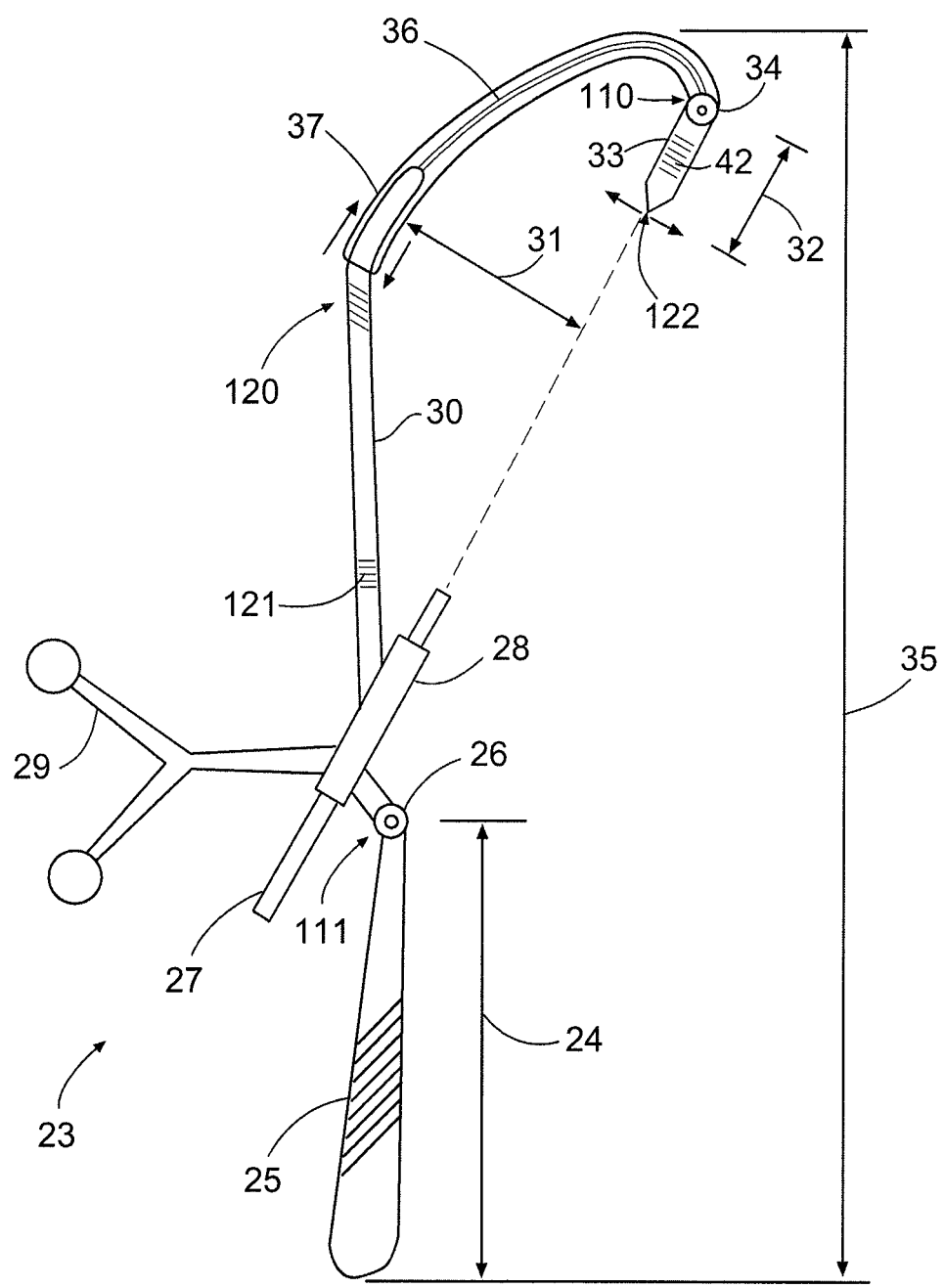
FIG. 2A shows a schematic view of an arthroscopic transfemoral guide pin placement jig configured for use in arthroscopic evaluations and treatments of the hip and having features of the invention including an adjustable intra-articular portion for the femoral head, adjustable arc of motion, computer aided navigation capability, and an adjustable extra-articular portion for the proximal femur.

An arthroscopic transfemoral guide pin placement jig device 23, as shown in FIG. 2A, typically includes a handle portion 25, a curved and elongated shaft portion 30, and a distal portion with a tip 33 that localizes a retrograde placed guide pin/wire 11 within the femoral neck 18 into the femoral head having features of the invention is illustrated in FIG. 2A. A handle portion 25 of the jig having features of the invention may be straight, or may be curved, and may include both straight and curved portions with cannula features. In embodiments, a handle portion 25 is rigid and contoured to allow precision grip by the surgical operator. The angle of the handle to the curved portion 26 may be adjustable or fixed angled (see, e.g., element 111) to facilitate use. A shaft portion of the guide wire/pin device having features of the invention may be straight, may be curved, may be adjustable, and may include both straight and curved portions with cannula features 28 and 27. In embodiments, a shaft portion 30 may be configured to be able to be bent or curved 37 by the hands of an operator, and to retain such bend or curve during use. Shaft 30 has a substantially cylindrical, elongated form, with a substantially circular cross section. A shaft 30 may be hollow, for example may be a hollow tube with a circular or oval cross-sectional shape. However, a shaft 30 of an arthroscopic jig 23 having features of the invention may have any suitable cross-sectional shape, including elliptical, triangular, square, rectangular, irregular, or may have another elongated configuration with any other cross-sectional shape. A tip portion of the device 33 having features of the invention is configured to be movable 34 with respect to other portions of the shaft, under the direction of the operator of the device. Changes in the radius of curvature or length of shaft curve will correct angles at the distal tip 110 to ensure guide pin placement at the tip via mechanical translation of the operators wishes by wire, rod, or hydraulic mechanics 36 to the jig tip. It will be understood that other mechanisms can also be used to control the amount of deflection of a tip portion 33 under control of an operator. Operative elements may be disposed on a distal portion of the device 33, and, in embodiments, may be disposed on a distal tip of the device. Computer aided surgical navigation markers 29 may be added to aspects of the device to ensure use and compatibility with surgical navigation systems. In embodiments, the length of the arthroscopic transfemoral guide pin placement jig 35 is about 120 mm to about 350 mm. The arc of curvature of the arthroscopic transfemoral guide pin placement jig 31 is about 20 mm to about 160 mm. The handle portion 24 of the arthroscopic transfemoral guide pin placement jig is about 120 mm to about 180 mm in length. The arthroscopic transfemoral guide pin placement jig tip portion 33 & 32 is about 5 mm to about 20 mm in length and about 2 mm to about 7 mm in diameter.

Figure 2B:
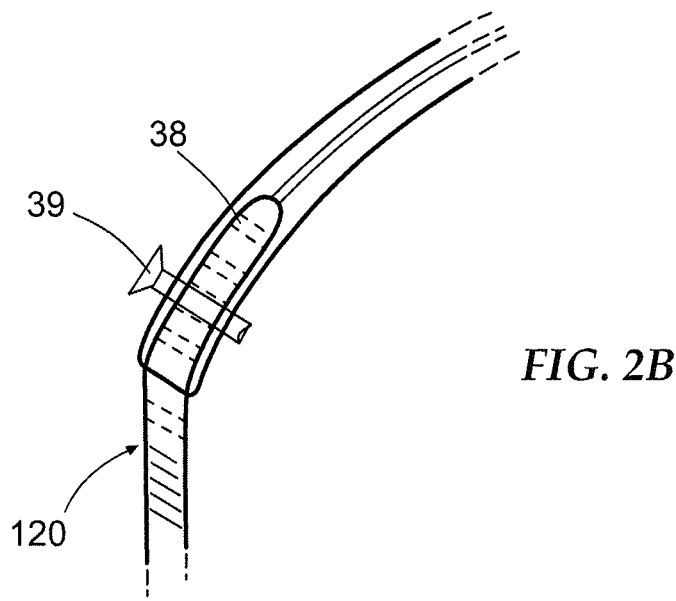
FIG. 2B is a schematic illustration of the adjustable mechanism for the arc of motion of an arthroscopic transfemoral guide pin placement jig of FIG. 2A in which a locking pin is shown.
Figure 2C:
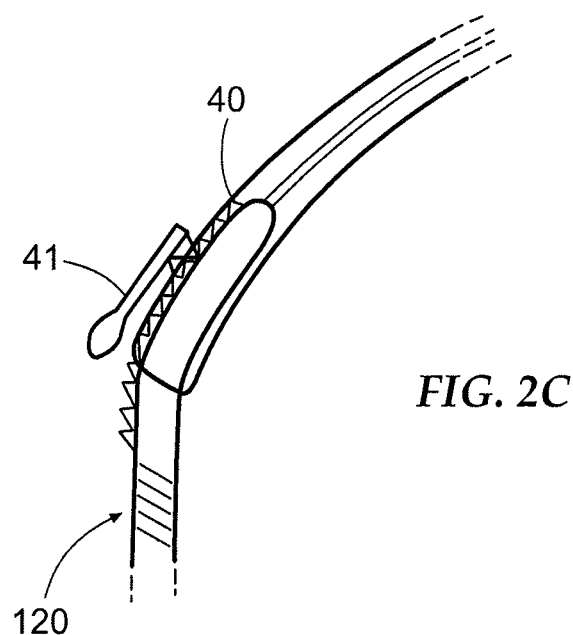
FIG. 2C is a schematic illustration of the adjustable mechanism for the arc of motion of an arthroscopic transfemoral guide pin placement jig of FIG. 2A in which a ratchet mechanism is shown.

As shown in FIGS. 2A, 2B, and 2C, an arthroscopic jig having features of the invention may have a mark 120 or markings 120 along a portion of a shaft 30, or along an entire shaft 121, and/or provided on a tip portion 42 or on the tip 122. Markings 120 & 42 are useful to aid an operator in determining the position or depth of the device or degree of deflection of the tip. Markings 120 & 42 are typically visible by eye by an operator or observer, although in embodiments, marks 120 & 42 may also be radiopaque or otherwise detectable by other than the human eye. Such markings may comprise colored portions of the shaft. Such markings may be all of a single color or may include multiple colors, and may be lines, bands, dots, geometric shapes, symbols, colors, combinations of these, or other indications detectable by an operator during use of an arthroscopic jig 23 having features of the invention. Markings 120 & 121 may completely encircle the shaft or may only extend about a part of a shaft circumference. Such markings are useful to aid an operator in judging the depth or position of the tip portion of the probe during use. Markings 120 may be useful, for example, to indicate the position of the tip 33 and tip portion 122 with respect to the skin surface of a patient into which the instrument has been inserted. In embodiments, where the shaft 30 is transparent or has a transparent portion allowing an operator to see a control rod 36 within the shaft, markings 120 may also be carried on the control rod 36 to aid an operator in determining the degree of tip deflection during operation of the device.

A flexible portion 34 of the shaft 30, part of the tip portion 33, allows for the movement of the tip 122. The flexible portion 34 may include gaps in portions of the shaft, a hinge, a pleated or accordion-type structure, a mesh, a flexible material, a combination of two or more of such elements for providing flexibility or movability, or other elements effective to allow or provide for movement of the tip.

FIG. 2B shows a section of an arthroscopic transfemoral guide pin placement jig 23 at the level of the shaft junction that controls the radius of curvature of the jig in which the junction is secured by a pin lock mechanism utilizing a screw, pin, or clip 39 that is placed into a adjoining smooth hole, threaded hole, or congruent hole 38 which maintains the arc of curvature desired by the operator of the device.

FIG. 2C shows a section of an arthroscopic transfemoral guide pin placement jig 23 at the level of the shaft junction that controls the radius of curvature of the jig in which the junction is secured by a ratchet mechanism utilizing a lever mechanism 41 to engage or release ratchet wedge from corresponding/mating teeth 40 on the shaft 30 insertion.

A shaft 30 of an arthroscopic jig 23 may be made of any suitable material, including metal, polymer, plastic, fiberglass, or other material or mixture of materials. A tip portion 33, which includes a flexible portion 34, may be made of any suitable material, including metal, polymer, plastic, fiberglass, or other material or mixture of materials, which have suitable flexibility. Such flexibility may be provided by providing appropriate wall thickness, by including, for example, gaps in the flexible portion 34, or by other modifications to the structure or material. It will be understood that, for a given material, smaller diameter and thinner walls typically provide greater flexibility than do thicker walls. Suitable metals for a shaft 30 and a tip portion 33 include stainless steel and nickel-titanium alloys, and suitable polymeric materials include polycarbonate, polyethylene, polyurethane, polyolefin, and other materials which may be used in fabrication of part or all of a shaft 30 or tip portion 33.

A retrocentripetal radial reamer device having features of the invention is illustrated in FIG. 3A. A shaft portion 46 of the retrocentripetal radial reamer device having features of the invention may be cannulated 45, may be straight, may be flexible, or may be straight and flexible. In embodiments, a shaft portion may be configured to be able to be bent or curved by the hands of an operator, and to retain such bend or curve during use. A proximal portion of the retrocentripetal radial reamer may be contoured 112 to allow detachment and attachment to hand held or robotic guided drill device. A distal tip portion of the retrocentripetal radial reamer device having features of the invention comprises two cutting wings 47 connected to distal reamer shaft or internal guide wire 11 by rotational axis 97. The cutting wings with inferior (caudal/distal facing) or superior (cranial/proximal) cutting surfaces are deployable by centripetal force or internal guide wire 11 to a shaft-blade angle between 0 and 90 degrees. In embodiment, the distal reamer tip may assume retracted, deployed, or enclosed positions. The length 43 of the retrocentripetal radial reamer device is about 150 mm to about 350 mm and the diameter 44 of the device is about 6 mm to about 18 mm. The internal cannula diameter 45 is about 2 mm to about 18 mm.

FIG. 3B shows a section of the retrocentripetal radial reamer device at the level of the distal tip with blades removed. Upon deployment, the blades exit from the bilateral slot 63 which is about 5 mm to about 20 mm in length 64 and about 1 mm to about 5 mm in width. The blades are maintained in relation to the distal tip of the retrocentripetal radial reamer device by a local axis 97.

A retrocentripetal radial reamer device having features of the invention is illustrated in FIG. 3C. A shaft portion 50 of the retrocentripetal radial reamer device having features of the invention may be cannulated 45, may be straight, may be flexible, or may be straight and flexible. In embodiments, a shaft portion may be configured to be able to be bent or curved by the hands of an operator, and to retain such bend or curve during use. A proximal portion of the retrocentripetal radial reamer may be contoured 112 to allow detachment and attachment to hand held or robotic guided drill device. A distal tip portion of the retrocentripetal radial reamer device in the deployed position having features of the invention comprises two cutting wing blades 55 connected to distal reamer shaft or internal guide wire 51 by rotational axis 97. The cutting wings with inferior 57 (caudal/distal facing) or superior 106 (cranial/proximal) cutting surfaces are deployable by centripetal force or internal guide wire 51 to a shaft-blade angle 108 between 0 and 90 degrees. In embodiment, the distal reamer tip may assume retracted, deployed, or enclosed positions. The length 43 of the retrocentripetal radial reamer device is about 150 mm to about 350 mm and the diameter 44 of the device is about 6 mm to about 20 mm. The length of a cutting wing blade 48 is about 15 mm to about 35 mm. The height of a cutting wing blade 49 is about 5 mm to about 16 mm. The width of a cutting wing blade 55 is about 0.5 mm to about 3 mm. The internal cannula diameter 45 is about 2 mm to about 18 mm.

An arthroscopic transfemoral retrocentripetal and antecentripetal radial reamer device having features of the invention is illustrated in FIGS. 3D, 3G, and 3H. A shaft portion 52 of the arthroscopic transfemoral retrocentripetal and antecentripetal radial reamer device having features of the invention may be cannulated 45, may be straight, may be flexible, or may be straight and flexible. In embodiments, a shaft portion may be configured to be able to be bent or curved by the hands of an operator, and to retain such bend or curve during use. A proximal portion of the retrocentripetal radial reamer may be contoured 112 to allow detachment and attachment to hand held or robotic guided drill device. A distal tip portion of the arthroscopic transfemoral retrocentripetal and antecentripetal radial reamer device in the deployed position (FIG. 3G) having features of the invention comprises a single cutting wing blade 56 connected to distal reamer shaft or internal guide wire 53 by internal couple 54 comprising a bi-lobed hole central to the cutting wing blade and a sliding bearing attached to distal reamer shaft or internal guide wire 53. The cutting wing with inferior 107 (caudal/distal facing) or superior 58 (cranial/proximal) cutting surfaces are deployable by centripetal force or internal guide wire 53 to a shaft-blade angle of 90 degrees. In embodiment, the distal reamer tip may assume retracted, deployed (FIG. 3G), or enclosed (FIG. 3D) positions. The length 43 of the arthroscopic transfemoral retrocentripetal and antecentripetal radial reamer device is about 150 mm to about 350 mm and the diameter 44 of the device is about 6 mm to about 20 mm. The length of a cutting wing blade 59 is about 15 mm to about 35 mm. The height of a cutting wing blade 60 is about 5 mm to about 16 mm. The width of a cutting wing blade 55 is about 0.5 mm to about 3 mm. The internal cannula diameter 45 is about 2 mm to about 18 mm.

FIGS. 3E and 3F shows a section of the arthroscopic transfemoral retrocentripetal and antecentripetal radial reamer device at the level of the distal tip with blade removed. Upon deployment, the blades exit from the bilateral slot 62 which is about 5 mm to about 20 mm in length 61 and about 1 mm to about 5 mm in width. The blade is maintained in relation to the distal tip of the arthroscopic transfemoral retrocentripetal and antecentripetal radial reamer device by bi-lobed couple 54 and link of distal reamer shaft or internal guide wire 53.

An acetabular shell prosthesis device having features of the invention is illustrated in FIGS. 4A and 4B. A removable shaft deployment tool 66 & 67 portion of the acetabular shell prosthesis device having features of the invention may be cannulated, may be straight, may be flexible, or may be straight and flexible. In embodiments, a shaft portion 67 may be configured to be able to be turned or manipulated by the hands of an operator to compress or deploy the arthroscopic transfemoral acetabular prosthesis 65. A collapsed 71 and expanded form 73 of the acetabular shell prosthesis device having features of the invention comprises a truss "Hoberman-type" hemisphere system that permits passage along the femoral neck access tunnel 22 and expansion into the prereamed area 17 along the acetabular side of the hip joint with locking mechanism across inner rings 114 to set diameter. In embodiment, the cephalad (pelvis side) surface 72 may contain an osteoinductive material cover of metal, plastic, ceramic, or biologic tissue and may tension across its outer circumference. An acetabular liner component 76 having features of the invention comprises a compressible or flexible construct that may be passed retrograde along the femoral neck 22 into the acetabular shell prosthesis 72 & 73. In embodiment, the acetabular liner outer diameter 78 is compatible with the inner diameter 115 of the acetabular shell prosthesis device, may interface with the acetabular shell prosthesis 72 &73 via a press fit configuration, local rim integration, or screw fixation. In its predeployed state, the outer diameter of the acetabular shell prosthesis 70 is about 6 mm to about 20 mm. The width of the acetabular shell cover 79 is about 1 mm to about 6 mm. The length of the predeployed arthroscopic transfemoral acetabular prosthesis 68 including deployment rod 67 is about 120 mm to about 300 mm. The length of the deployment rod 67 is about 119 mm to about 199 mm. The length of the deployment sheath 69 is about 109 mm to about 189 mm. The diameter of the deployment rod 67 is about 2 mm to about 7 mm. The diameter of the deployment sheath 66 is about 2.5 mm to about 7.5 mm. The "Hoberman-type" hemisphere system 71 & 73 is composed of 4 to 12 radial trusses that retract and extend based on the position of the deployment sheath 66.

An acetabular liner prosthesis device having features of the invention is illustrated in FIGS. 4C and 4D. In its deployed state, the outer diameter of the acetabular shell prosthesis 74 & 82 (FIG. 4B) is about 30 mm to about 65 mm. The height of the acetabular shell prosthesis 75 & 81 (FIG. 4B) is about 15 mm to about 33 mm. The acetabular liner prosthesis device (FIG. 4C) has complementary dimensions including an outer diameter 78 of about 29 mm to about 64 mm, a height 77 of about 14.5 mm to about 32 mm, and a wall thickness 80 of 2 mm to 10 mm. The acetabular liner convex surface material 116 is compatible with the deployed truss system 73 and attaches via adhesion, mechanical or chemical integration, press/wedge fit, or cold welding. The acetabular liner convex surface material may be plastic, metal, ceramic, polymer, resin, engineered tissue, or combination of two or more. The acetabular liner concave surface material 76 is compatible with the femoral prosthesis surface material 94. The acetabular liner concave surface material 76 may be plastic, metal, ceramic, polymer, resin, engineered tissue, or combination of two or more.

A femoral head prosthesis device having features of the invention is illustrated in FIGS. 5A, 5B, and 5C. A removable shaft deployment tool 84 & 85 portion of the femoral head prosthesis device having features of the invention may be cannulated, may be straight, may be flexible, or may be straight and flexible. In embodiments, a shaft portion 84 may be configured to be able to be turned or manipulated by the hands of an operator to compress or deploy the femoral head prosthesis 83. A collapsed 88 and expanded form 91 of the femoral head prosthesis device having features of the invention comprises a truss "Hoberman-type" hemisphere system that permits passage across the femoral neck access tunnel 22 and expansion into the prereamed area 14,15,&16 along the femoral head and neck side of the hip joint with locking mechanism across inner rings 116 to set diameter 92 & 95. In embodiment, the caudal/distal (truss side) surface 91 may contain an osteoinductive material coating of metal, plastic, ceramic, or biologic tissue and may tension across its outer circumference. A femoral head surface component 94 having features of the invention comprises a compressible or flexible construct that may be passed retrograde along the femoral neck 22 attached to the supportive truss system. In embodiment, the femoral head prosthesis outer diameter 92 & 95 is compatible with the inner diameter 118 of the acetabular shell prosthesis device. Additionally, the femoral head prosthesis outer height 93 & 96 is compatible with the inner height (radius) 119 of the acetabular prosthesis. The femoral head inner diameter 117 interfaces with the femoral osteotomy area 14, 15, & 16 via a press fit configuration, tension banding across fixation lateral to transfemoral access 22, local PMMA/adhesives/biologics, or screw fixation. In its predeployed state 90, the outer diameter of the femoral head prosthesis (FIG. 5A) is about 6 mm to about 20 mm. The width of the femoral head surface 89 is about 1 mm to about 6 mm. The length of the predeployed femoral head prosthesis 87 including deployment rod 87 is about 110 mm to about 290 mm. The length of the deployment rod 84 is about 109 mm to about 189 mm. The length of the deployment sheath 86 is about 99 mm to about 179 mm. The diameter of the deployment rod 84 is about 2 mm to about 7 mm. The diameter of the deployment sheath 85 is about 2.5 mm to about 7.5 mm. The "Hoberman-type" hemisphere system 88 & 91 is composed of 4 to 12 radial trusses that retract and extend based on the position of the deployment sheath 85.

A femoral head prosthesis device having features of the invention is illustrated in FIGS. 5A-5C. A removable shaft deployment tool portion of the femoral head prosthesis device having features of the invention may be cannulated, may be straight, may be flexible, or may be straight and flexible. In embodiments, a shaft portion may be configured to be able to be turned or manipulated by the hands of an operator to compress or deploy the femoral head prosthesis. A collapsed and expanded form of the femoral head prosthesis device having features of the invention comprises a truss "Hoberman-type" hemisphere system that permits passage across the femoral neck access tunnel and expansion onto the prereamed area along the femoral head side of the hip joint with locking mechanism across inner radial arms to set diameter. In embodiment, the cephalad (pelvis side) surface may contain a material cover of metal, plastic, ceramic, or biologic tissue and may tension across its outer circumference. In embodiment, the femoral head prosthesis may be stabilized with rods, wires, or sutures to the bone of the proximal femur along the neck. In embodiment, the space between the femoral head prosthesis and the femoral side bone may be back-filled with osteoconductive matrix, polymer, or polymethylmethacrylate (PMMA).

Although cannulas are not required for surgical joint access, some surgeons may prefer to access the joint via cannulas. An arthroscopic transfemoral guide pin gig, arthroscopic transfemoral antecentripetal and retrocentripetal radial reamer, arthroscopic transfemoral acetabular shell prosthesis, and arthroscopic transfemoral femoral head prosthesis having features of the invention may be used with an access cannula, or may be used without using an access cannula. A cannula optionally may be provided in a system having features of the invention, for use in situations where a cannula may be helpful, and by those surgeons who prefer to use a cannula in arthroscopic procedures. Thus, in embodiments of the methods of the invention, methods such as those discussed above may further include steps of providing a cannula, placing a cannula in position in a patient, and inserting a device having features of the invention into a cannula effective to position the tip of the device at a desired location within a patient.

Such methods including a cannula therefore may include, for example, the following steps:
a) placing a cannula in position in a patient;
b) inserting a hip gig, reamer, or prosthesis into said cannula;
c) inserting said hip gig, reamer, or prosthesis in said cannula into a patient near a hip joint of the patient.

Thus, while particular forms of the invention have been illustrated and described, it will be apparent that various modifications can be made without departing from the spirit and scope of the invention. Accordingly, it is not intended that the invention be limited, except as by the appended claims. Reference to the terms "members," "elements," "sections," "portions," and terms of similar import in the claims which follow shall not be interpreted to invoke the provisions of 35 U.S.C. §112(paragraph 6) unless reference is expressly made to the term "means" followed by an intended function.

What is claimed is:

1. A system for performing an arthroscopic arthroplasty procedure with respect to a distracted hip joint of a human patient, the hip joint being defined by a femoral head extending from a femoral neck of a femur, and an acetabulum of a pelvis, said system comprising:
an acetabular prosthesis and a complementarily-configured femoral head prosthesis, each of the prostheses being configured to be directed through a channel defined by and extending along a longitudinal axis of and through the femoral neck, and through the femoral head, for insertion into the distracted hip joint, the channel having a smaller width than a maximum width of the femoral neck and either of the prostheses, the femoral head having a larger width than the maximum width of the femoral neck, and the prostheses each being further configured to be deployed within the distracted hip joint, from the channel, into engagement with the corresponding one of the acetabulum and the femoral head of the distracted hip joint, the acetabular prosthesis being configured to receive the femoral head prosthesis upon non-distraction of the distracted hip joint.

2. A system according to claim 1, further comprising a joint preparation device configured to extend through the channel into the distracted hip joint; the joint preparation device being configured to osteotomize one of the femoral head and the acetabulum for receiving the respective one of the femoral head prosthesis and the acetabular prosthesis, prior to the application thereof.

3. A system according to claim 1 further comprising a distraction device adapted to be engaged between the femur and the pelvis, and operable to distract the hip joint, to form the distracted hip joint, by separating the femoral head from the acetabulum.

4. A system according to claim 3, further comprising an alignment device adapted to be engaged between the femur and the pelvis and operable to maintain the distracted hip joint in accordance with a normal hip joint alignment.

5. A system according to claim 1, further comprising a jig device adapted to be aligned along the femoral neck of the femur, the jig device being configured to receive a boring device and to guide the boring device for boring the channel through the femoral neck and the femoral head toward the acetabulum.

6. A system according to claim 5, wherein the jig device further comprises:
a cannulated element adapted to interact with the femoral neck opposite the femoral head, and being configured to receive the boring device therethrough;
a guide tip portion adapted to engage the femoral head in opposition to the cannulated element, the cannulated element and guide tip portion being aligned along the longitudinal axis of the femoral neck; and
a frame element operably engaged between the cannulated element and the guide tip portion, the frame element being configured to be adjustable so as to vary a length between the cannulated element and the guide tip portion, and a deflection angle of the guide tip portion with respect to the longitudinal axis.

7. A system according to claim 6, wherein the frame element further comprises a first frame portion operably engaged with the guide tip portion and a second frame portion operably engaged with the cannulated element, the first and second frame portions being configured to adjustably engage each other along an at least partially arcuate engagement path for varying the length and deflection angle.

8. A system according to claim 7, further comprising a securement device operably engaged between the first and second frame portions, the securement device being configured to selectively secure the first and second frame element with respect to each other upon attaining a desired length and deflection angle.

9. A system according to claim 6, wherein the jig device further comprises at least one alignment element capable of being detected by one of a computer device and an imaging system to facilitate placement of one of the cannulated element and the guide tip portion with respect to the femoral neck.

10. A system according to claim 2, wherein the joint preparation device further comprises at least one reaming blade, the at least one reaming blade being capable of being inserted into the hip joint through the channel and having a shaft element associated therewith, the shaft element being configured to cooperate with the at least one reaming blade so as to rotate the at least one reaming blade about the longitudinal axis of the femoral neck to osteotomize one of the femoral head and the acetabulum for receiving the respective one of the femoral head prosthesis and the acetabular prosthesis.

11. A system according to claim 10, wherein the shaft element further comprises an elongate cannula member configured to extend through the channel and into the hip joint, the cannula member having a proximal end and a distal end, the distal end being configured to house at least one reaming blade coupled to a control member, the control member extending from the at least one reaming blade along the cannula member and through the proximal end thereof, the at least one reaming blade being deployable into the hip joint by longitudinal extension of the control member to direct the at least one reaming blade out of the cannula member, and manipulation of the control member to extend the at least one reaming blade laterally outward of the longitudinal axis, for subsequent rotation thereof about the longitudinal axis.

12. A system according to claim 11, wherein the at least one reaming blade, extended laterally outward of the longitudinal axis, is further configured to be rotatable about the longitudinal axis, by rotation of one of the control member and the cannula member, for osteotomizing one of the femoral head and the acetabulum for receiving the respective one of the femoral head prosthesis and the acetabular prosthesis.

13. A system according to claim 12, wherein the at least one reaming blade is configured to be rotatable through rotation of the cannula member, and wherein the distal end of the cannula member defines opposed slots extending parallel to the longitudinal axis, the slots being configured to receive the at least one reaming blade, extended laterally outward of the longitudinal axis, upon retraction of the control member through the channel, and to secure the at least one reaming blade to the cannula member so as to allow the cannula member to rotate the at least one reaming blade.

14. A system according to claim 10, wherein the at least one reaming blade includes a proximal blade portion configured to be rotated about the longitudinal axis to osteotomize the acetabulum for receiving the acetabular prosthesis.

15. A system according to claim 10, wherein the at least one reaming blade includes a proximal blade portion configured to be rotated about the longitudinal axis to osteotomize the femoral head for receiving the femoral head prosthesis.

16. A system according to claim 10, wherein the joint preparation device is configured to be retractable from the hip joint through the channel defined by the femoral neck.

17. A system according to claim 1 wherein the acetabular prosthesis further comprises an acetabular shell portion expandable into a substantially hemispherical shell configuration corresponding to the osteotomized acetabulum for receipt thereby.

18. A system according to claim 17, wherein the acetabular prosthesis further comprises an expandable hemispheric truss device operably engaged with the acetabular shell portion, the hemispheric truss device being configured to cooperate with the acetabular shell portion so as to expand the acetabular shell portion within the osteotomized acetabulum such that the acetabular shell portion is disposed between the osteotomized acetabulum and the hemispheric truss device.

19. A system according to claim 18, further comprising an acetabular prosthesis placement element including an acetabular prosthesis cannula element configured to receive the acetabular shell portion having the hemispheric truss device operably engaged therewith, the acetabular prosthesis cannula element being configured to carry the acetabular shell portion and the hemispheric truss device to the osteotomized acetabulum, the hemispheric truss device being coupled to a deployment device configured to expand the hemispheric truss device and the acetabular shell portion operably engaged therewith, within the osteotomized acetabulum.

20. A system according to claim 18, wherein the acetabular prosthesis further comprises an acetabular liner portion expandable into a substantially hemispherical shell configuration corresponding to the acetabular shell portion having the hemispheric truss device therein, for receipt thereby, such that the hemispheric truss device is disposed between the acetabular shell portion and the acetabular liner portion.

21. A system according to claim 1, wherein the femoral head prosthesis further comprises a femoral head shell portion expandable into a substantially hemispherical shell configuration corresponding to the acetabular liner portion of the acetabular prosthesis, for receipt thereby upon removal of the distraction device from the hip joint.

22. A system according to claim 21, wherein the femoral head prosthesis further comprises an expandable hemispheric truss device operably engaged with the femoral head shell portion, the hemispheric truss device being configured to cooperate with the femoral head shell portion so as to expand the femoral head shell portion to extend over the osteotomized femoral head such that the hemispheric truss device is disposed between the osteotomized femoral head and the femoral head shell portion.

23. A system according to claim 22, further comprising a femoral head prosthesis placement element including a femoral head prosthesis cannula element configured to receive the femoral head shell portion having the hemispheric truss device operably engaged therewith, the femoral head prosthesis cannula element being configured to carry the femoral head shell portion and the hemispheric truss device to the osteotomized femoral head, the hemispheric truss device being coupled to a deployment device configured to expand the hemispheric truss device and the femoral head shell portion operably engaged therewith, within the hip joint.

24. A system according to claim 23, wherein the deployment device is operably engaged with at least the hemispheric truss device, and the hemispheric truss device having the femoral head shell portion operably engaged therewith is configured to engage the osteotomized femoral head upon retraction of the deployment device along the channel outwardly of the hip joint such that the hemispheric truss device is disposed between the osteotomized femoral head and the femoral head shell portion.

25. A system according to claim 24, further comprising a prosthesis securement element configured to operably engage the deployment device about an entrance to the channel defined by the femoral neck so as to secure the femoral head prosthesis to the osteotomized femoral head.

26. A system according to claim 1, wherein the alignment device further comprises at least one alignment element capable of being detected by one of a computer device and an imaging system to facilitate maintenance of the distracted hip joint in accordance with a normal hip joint alignment.

* * * * *